(12) United States Patent
Jacobi et al.

(10) Patent No.: US 6,277,277 B1
(45) Date of Patent: Aug. 21, 2001

(54) CARTRIDGE HOLDER FOR A DIALYZING MACHINE

(75) Inventors: Juergen Jacobi; Robert Mardorf, both of Melsungen (DE)

(73) Assignee: B. Braun Melsungen AG, Melsungen (DE)

( * ) Notice: Subject to any disclaimer, the term of this patent is extended or adjusted under 35 U.S.C. 154(b) by 0 days.

(21) Appl. No.: 09/576,275

(22) Filed: May 24, 2000

(30) Foreign Application Priority Data

Jun. 2, 1999 (DE) .............................................. 199 25 297

(51) Int. Cl.⁷ ............................ B01D 61/30; B01D 65/00
(52) U.S. Cl. ......................... 210/240; 210/232; 210/239
(58) Field of Search .................................. 210/232, 235, 210/237, 239, 240, 645, 646

(56) References Cited

U.S. PATENT DOCUMENTS 5,641,144 * 6/1997 Hendrickson et al. ......... 248/292.13
5,770,064 * 6/1998 Jonsson et al. ...................... 210/232
6,050,278 * 4/2000 Arnal et al. .......................... 210/646

* cited by examiner

*Primary Examiner*—John Kim
(74) *Attorney, Agent, or Firm*—Diller, Ramik & Wigh

(57) ABSTRACT

A dialyzing machine is provided with a cartridge holder to which a filter cartridge (11) or a dialyzer cartridge can be fastened. The cartridge holder (25) comprises a holding element (35) retaining the cartridge (11) and a clamping element (36) which is movable relatively to the holding element and radially to the inserted cartridge. The clamping element can be moved from an open position into a closed position. It comprises two connecting members (41,42) cooperating with the lateral connecting studs (26,27) of the cartridge, the connecting members (41,42) sealingly engaging with the two connecting studs (26,27) of the cartridge when the clamping element (36) is moved into the closed position. In this way a connection with the two connecting studs of the cartridge is produced by simply attaching the cartridge to the cartridge holder. It is no longer necessary to individually connect hoses to the connecting studs.

11 Claims, 4 Drawing Sheets

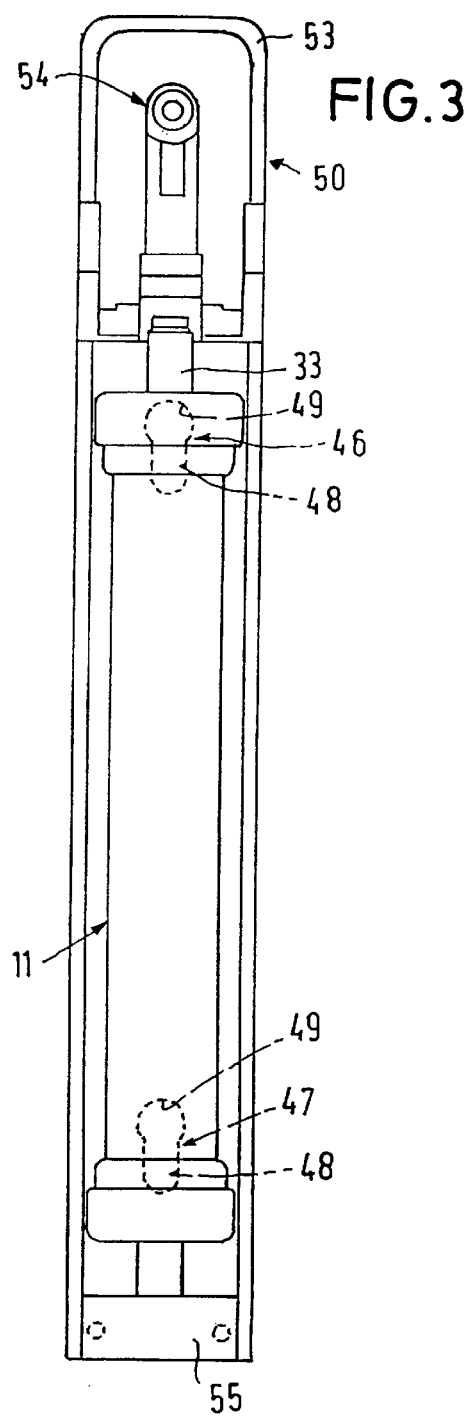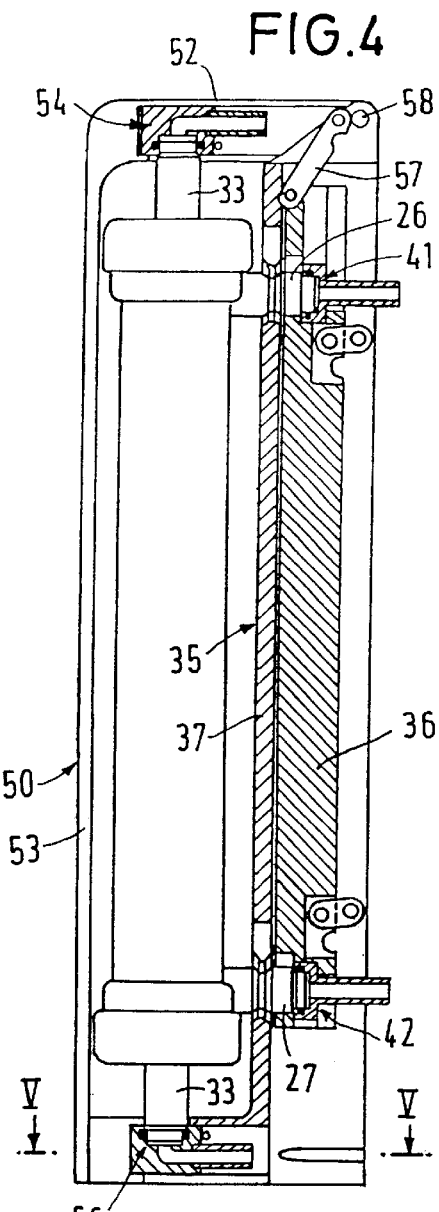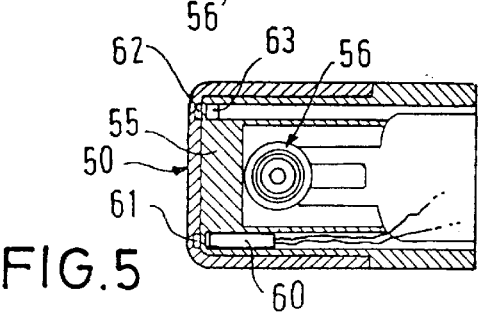

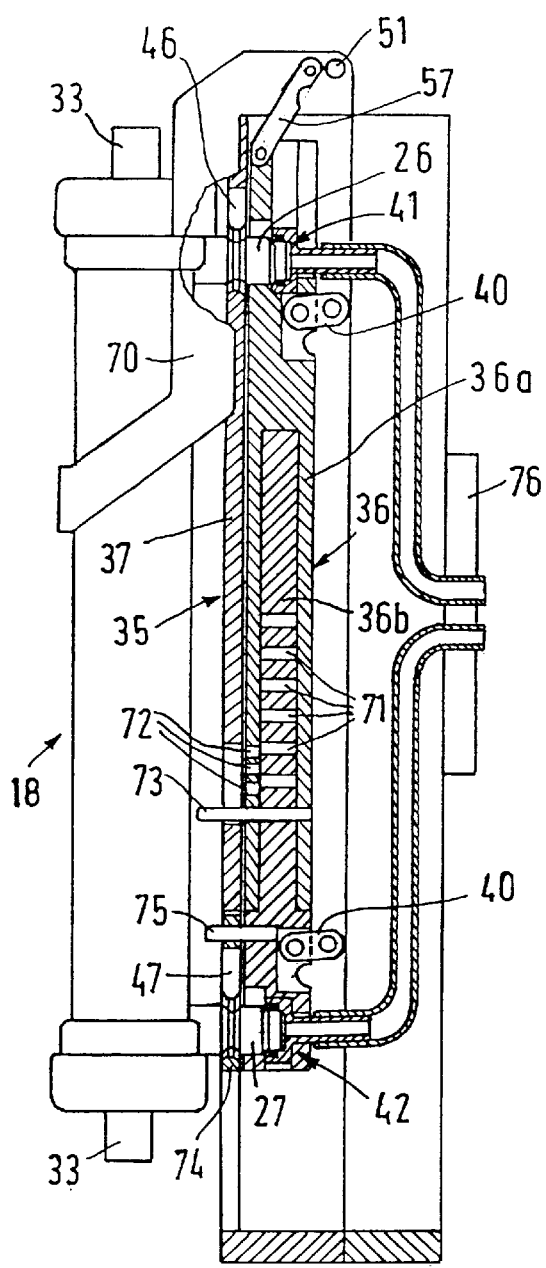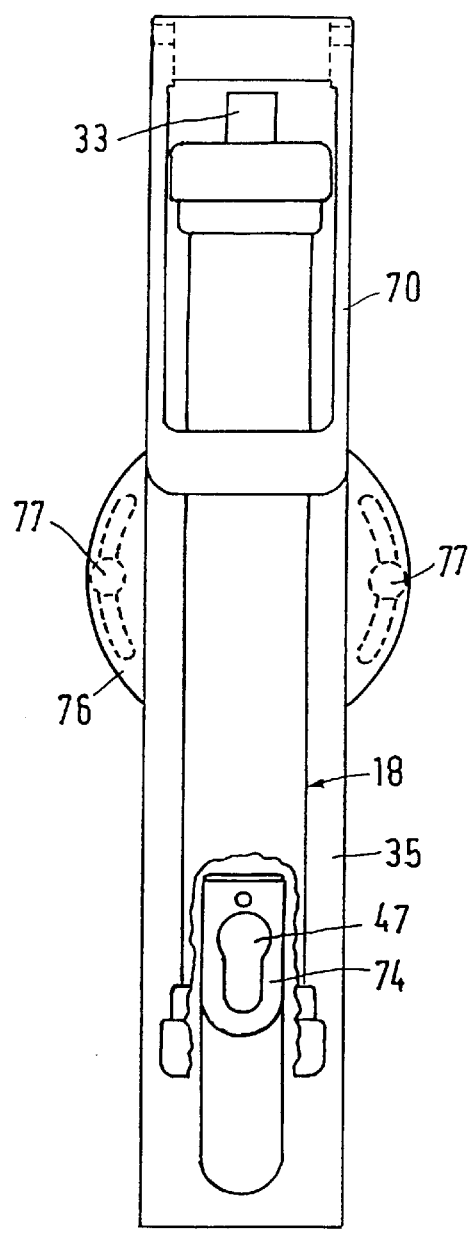

FIG. 9
FIG. 8
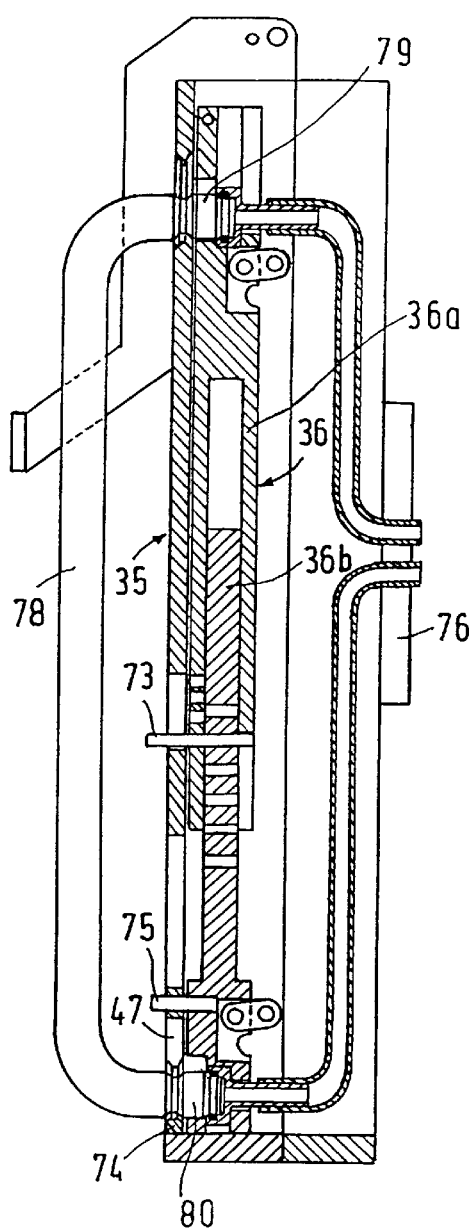
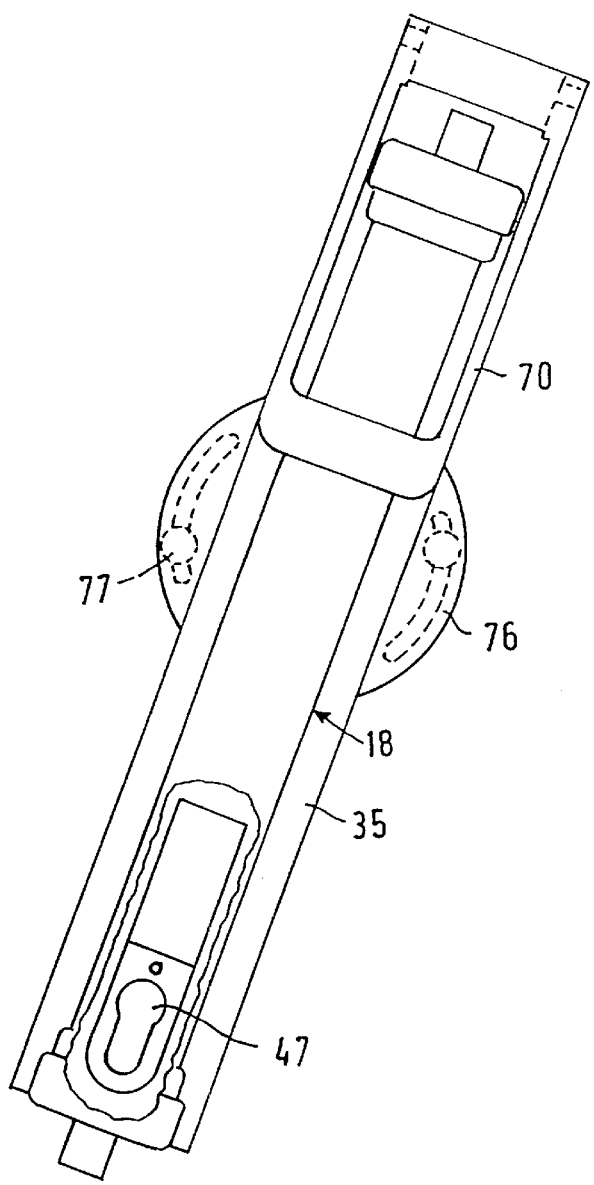

US 6,277,277 B1

CARTRIDGE HOLDER FOR A DIALYZING MACHINE

BACKGROUND OF THE INVENTION

The present invention relates to a cartridge holder for a dialyzing machine designed for fastening and connecting a cartridge which contains a filter or a dialyzer.

Dialyzing machines need at least one filter for fine filtering a haemodialysis solution before said solution is fed to the dialyzer. Said filter is normally configured as a hollow fibre filter contained in a cartridge. The cartridge comprises two axial connecting studs located at opposite ends, which connecting studs are connected to the supply line, and two connecting studs laterally projecting from the cylindrical cartridge body, which connecting studs are interconnected and form the filtrate outlet leading to the dialyzer. Said dialyzer also comprises hollow fibres arranged in a cartridge. The dialysate path leads through two connecting studs laterally projecting from the cartridge body, and the blood path leads axially through the cartridge. Normally the filter cartridge and the dialyzer cartridge are connected with corresponding hose lines of the dialyzing machine. Since the filter and the dialyzer require a total of eight connections it may happen that hose lines are incorrectly connected which may have fatal consequences. Further, change of the filter or the dialyzer involves relatively great efforts.

It is an object of the present invention to provide a cartridge holder for a dialyzing machine, the cartridge holder facilitating connection of a cartridge to the dialyzing machine and precluding incorrect connections.

SUMMARY OF THE INVENTION

The cartridge holder according to the invention comprises on the one hand a holding element retaining the cartridge in a defined position and on the other hand a clamping element sealingly connecting two connecting members with the lateral connecting studs of the cartridge when brought from an open position into the closed position. In the case of the cartridge holder according to the invention it is thus no longer necessary to push hose lines individually onto the connecting branches of the cartridge. The cartridge is rather retained by the holding element and the connections are simultaneously produced by the clamping element. Thus the cartridge needs only to be inserted into the cartridge holder, and subsequently the clamping element must be actuated. Manipulation of the connecting studs of the cartridge is no longer required. Further, there is no danger of confusing the lines since the lines are permanently fixed to the corresponding connecting members of the cartridge holder in the works and the user needs not to manipulate the lines at all.

The invention is suitable for both cartridge holders for filter cartridges and cartridge holders for dialyzer cartridges. However, in both cases the cartridge sizes may vary from each other but the connection principle is in both cases substantially the same. Filter cartridges and dialyzer cartridges differ from each other in that filter cartridges comprise four identical connecting studs whereas in dialyzer cartridges the connecting studs for the blood circulation are configured in a different way as compared with those for the haemodialysis solution. According to the invention the two lateral connecting studs of the cartridge are simultaneously connected with the corresponding connecting members via a closing action effected by an automatic connecting device. Here, the ends of the connecting studs are pushed into sealing rings of the connecting members.

The holding element retaining the cartridge during the coupling process and in the coupled condition preferably comprises holding openings for engaging with the connecting studs of the cartridge. Said holding openings are configured as keyhole openings and they are designed such that their edges protrude into grooves provided in the connecting studs of the cartridge so as to protect the cartridge against being pulled out. The cartridge is removed by being shifted inside the keyhole opening until the the connecting studs reach the wider head area of the keyhole opening from where they can be pulled out.

According to a preferred embodiment of the invention the clamping element is movable via a swivel bar articulated to the holding element, which swivel bar locks the inserted cartridge in its closed position. The swivel bar protects the cartridge from being unintentionally pulled out of the cartridge holder as well as against any other movement of the cartridge.

The cartridge holder may be configured such that it does not only make the connection with the lateral connecting studs of the cartridge but also the connection with the axial connecting studs. For this purpose a connecting member for an axial connecting stud is appropriately integrated in the swivel bar. When the swivel bar is closed the axial connecting member sealingly engages with the corresponding connecting stud of the cartridge. At the opposite end of the cartridge a supporting device is provided which comprises another connecting member for an axial connecting stud of the cartridge.

BRIEF DESCRIPTION OF THE DRAWINGS

Hereunder embodiments of the invention are explained in detail with reference to the drawings in which:

FIG. 3 shows a front view of FIG. 2 as seen in the direction of arrow III, FIG. 4 shows the same representation as FIG. 2 of the cartridge holder in operating condition with the swivel bar in the closed position, FIG. 5 shows a section along line V—V of FIG. 4, FIG. 6 shows a part-sectional side view a cartridge holder for a dialyzer cartridge, FIG. 7 shows a front view of the cartridge holder of FIG. 6, FIG. 8 shows the same representation of the cartridge holder as FIG. 7 with the cartridge holder in tilted position for the purpose of examining for bubbles, and FIG. 9 shows the cartridge holder of FIGS. 6–8 in the extended condition and with a short-circuit bar connecting the connecting members.

DESCRIPTION OF THE PREFERRED EMBODIMENTS

Figure 1:
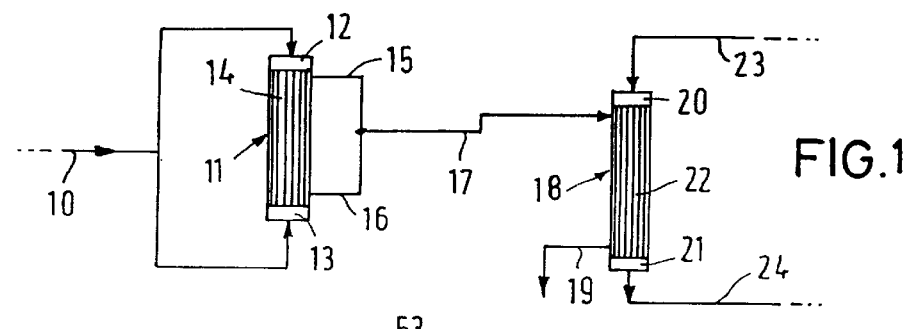
FIG. 1 shows a schematic flow chart of a filter and a dialyzer in a dialyzing machine.
Figure 2:
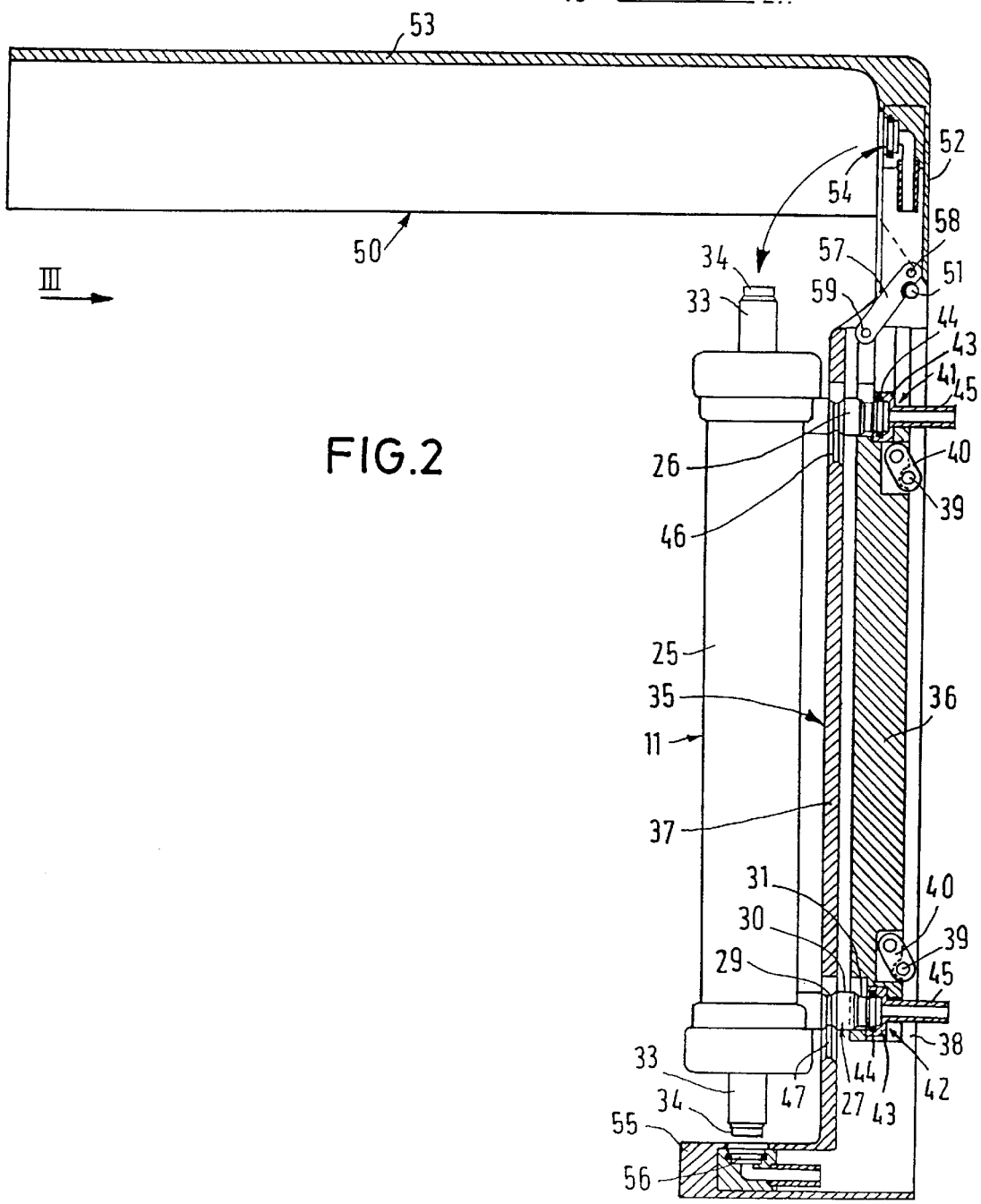
FIG. 2 shows a vertical section of a cartridge holder with inserted cartridge in the open position of the former.

FIG. 1 show a schematic respresentation of a part of the dialysate path and the blood path of a dialyzing machine. The haemodialysis solution is supplied via a line 10 to the opposing end sides of a filter cartridge 11. The filter cartridge contains at its one end a chamber 12 and at the other end a chamber 13. Between said chambers 12,13 a hollow fibre bundle 14 extends through whose hollow fibres the haemodialysis solution flows. The hollow fibre walls are permeable to the haemodialysis solution but not to particles contained therein. The cartridge 11 comprises two lateral outlets 15,16 which are connected with each other and via a line 17 with a lateral connection of the dialyzer cartridge 18. The haemodialysis solution flows along the hollow fibres and is branched off by a lateral connection 19. The dialyzer cartridge 18 also comprises a chamber 20 and 21 respectively at each end. Between said chambers hollow fibres 22 extend. The blood is supplied from the patient's body via the supply line 23 and leaves the dialyzer through the discharge line 24.

FIGS. 2 to 5 show a cartridge holder for a filter cartridge 11, the cartridge holder being fixed to a dialyzing machine (not shown). The filter catridged 11 comprises a tubular cartridge body 25 provided with two lateral connecting studs 26,27. Said connecting studs are identical to each other. They comprise a circumferential groove 29 near the cartridge body, adjacent to which groove a portion 30 enlarging towards the outside is provided. The outer end of the connecting stud forms a cylindrical sealing surface 31 of a smaller diameter than that of the enlarged portion 30.

The filter cartridge 11 further comprises two axial connecting studs 32,33 each provided at its end with a cylindrical sealing surface 34 of a reduced diameter.

The cartridge holder comprises a holding element 35 which forms a carrying and holding device and to which a clamping element 36 can be movably fastened. The holding element 35 is generally U-shaped and comprises a front plate 37 and lateral legs 38. Inside the holding element 35 the clamping element 36 made up of a plate is arranged. Between the legs 38 axes 39 extend on each of which a link 40 is supported. The other end of the link 40 is articulately connected with the clamping element 36. In this way the holding element 35, the clamping element 36 and the links 40 form a parallelogram linkage. The clamping element 36 can be tilted relatively to the holding element 35 with its parallel orientation being maintained with the clamping element 36 approaching the front plate 37 or moving away from the front plate 37.

The clamping element 36 carries two connecting members 41,42. Each connecting member comprises a holder 43 with an inserted sealing ring 44 into which the cylindrical sealing surface 31 of the connecting stud 26 and 27 respectively can be sealingly inserted. At its rear end the holder 43 is provided with a hose connection 45 projecting rearwardly.

The front plate 37 of the holding element 35 is provided with holding openings 46,47 which are configured as keyholes. This means that each holding opening has a relatively narrow vertical slot 48 and a wider circular head opening 49 (FIG. 3). The head opening 49 serves for receiving the lateral connecting stud 26 and 27 respectively, and the slot 48 is wide enough so that its slot edges engage with the groove 29 of the connecting stud thus fixing the connecting stud in axial direction. The cartridge is inserted such that the two connecting studs 26,27 are threaded through the head opening 49, and subsequently the cartridge is pulled down to be fixed in the slot 48. After this fixing process the clamping element 36 is moved towards the front plate 37 (FIG. 4) such that the holders 43 are pushed, together with the sealing rings 44, over the sealing surfaces 31 of the connecting studs. Thereby the connecting studs are fixed in each direction.

The horizontal parallel movement of the clamping element 36 is effected by a swivel bar 50 which can be swivelled about a horizontal axis 51 at the upper end of the holding element 35. The swivel bar 50 is L-shaped and comprises a short top leg 52 adjacent to the axis 51 and a longitudinal leg 53 with a U-shaped cross-section, the longitudinal leg 53 projecting at right angles form the top leg 52. In the swivelled-down condition (FIG. 4) the longitudinal leg 53 encloses the cartridge 11 on three sides. On the fourth side the cartridge is enclosed by the holding element. The swivel bar 50 extends over the overall cartridge length. The top leg 52 of the swivel bar 50 comprises a connecting member 54 which is similarly configured as the connecting members 41 and 42. Upon closing of the swivel bar 50 the connecting member 54 is tilted by 90° and pushed with vertical axis onto the end of the connecting stud 33 of the cartridge. The swivel bar 50 is also configured as heat protection hood which reduces temperature losses in particular during the disinfection process.

The holding element 35 ist provided at its lower end with a projecting supporting device 44 comprising another connecting member for the connecting stud 33 of the cartridge. The connecting member 56 is aligned with vertical axis. When the swivel bar 50 is in the open position the lower connecting stud 33 is located at an axial distance above the connecting element 56.

The clamping element 36 is controlled by a link 57 which is connected with the swivel bar 50 via an articulation 58 and with the clamping element 36 via an articulation 59. When the swivel bar 50 is closed the clamping element 36 is pushed down via the link 57. The tilted links 40 induce the clamping element 36 to perform a forward movement towards the front plate 37. During this process the holders 41,42 are pushed onto the ends of the connecting studs 26,27. Further, the connecting studs are moved down in the respective holding openings 46,47 in the area of the slot 48.

FIG. 5 shows the U-shaped swivel bar 50 in the closed condition in which its lower end encloses the supporting device 55. In the supporting device 55 a magnetic sensor 60 is provided which responses to a magnet 61 of the swivel bar 50 thus detecting the closing condition of the swivel bar. The sensor 60 allows the dialyzing machine to be operated only when the swivel bar is closed. In the swivel bar 50 and in the supporting device 55 magnets 62,63 are arranged which pull the swivel bar into the closed position.

For insertion purposes the cartridge 11 is threaded, with the connecting studs 26,27, through the head openings 49 of the keyhole-shaped holding openings 46,47 while the clamping element 36 is in the retracting position when the swivel bar 50 is open. Then the cartridge 11 is pressed down so that the connecting studs 26,27 reach the area of the slots 48 and are then positioned in axial alignment with the respective connecting member 41,42. In this condition the swivel bar 50 is swivelled from the open position into the closed position. During this process the clamping device 36 is also advanced into the closed position. The connecting members 41,42 are pushed onto the connecting studs 26,27, and the connecting studs in the respective holding opening 46,47 are moved further down in the slot 48. During this downward movement the lower axial connecting stud 33 is inserted into the corresponding connecting member 56 of the supporting device 55. At the end of the swivel movement of the swivel bar the upper connecting member 54 is sealingly pushed onto the upper connecting stud 33 of the cartridge. Now all connecting studs are sealingly connected with the respective connecting members, and the cartridge can be taken into operation.

FIGS. 6–9 show a cartridge holder for a dialyzer cartridge 18. Those parts which correspond to those of the first embodiment bear the same reference numerals. The following description is limited to the explanation of the differences.

In contrast to the filter cartridge, in the case of the dialyzer cartridge only the two lateral connecting studs 26,27 of the cartridge holder are connected while the axial connecting studs 33 are manually connected to the corresponding hose lines. Thus the swivel bar 70 is of smaller configuration in the present embodiment so that it surrounds the cartridge 18 from three sides as seen from above but extends only over a part of the cartridge length. Here too, the swivel bar 70 controls the movement of the clamping element 36 which is connected via links 40 with the holding element 35.

In the present embodiment the clamping element 36 is adjustable in length. For this purpose a slide 36b is inserted into a body 36a of the clamping element. The slide is provided with a plurality of holes 71 each of which can be aligned with a counterhole 72 in the body 36a and fixed by inserting a guide pin 73. At the lower end of the slide 36b the connecting member 42 is arranged and at this end the lower link 40 engages. FIG. 6 shows the clamping element in the retracted condition and FIG. 9 shows the clamping element in the extended position. At the lower end of the slide 36b a carrier 74 is located upstream of the connecting member 42, at which carrier 74 the lower holding opening 47 is located. Said carrier is coupled via a carrier pin 75 with the lower part of the slide 36b such that the holding opening 47 is always located upstream of the lower connecting member 42.

On the rear side of the holding element 35 a swivel device 76 is arranged which is fastened by bolts 77 to the housing of the dialyzing machine. By loosening the bolts 77 the entire cartridge holder can be swivelled about a horizontal transverse axis. This serves the purpose of detecting air bubbles in the transparent cartridge 18 by visual inspection. In the operating condition the cartridge holder is brought into the vertical position shown in FIGS. 6 and 7.

FIG. 9 shows the cartridge holder in the extended condition. Here, no cartridge is inserted in the holding element but a short-circuit bar 78 with connecting studs 79 and 80 provided at its ends, the connecting studs 79 and 80 being configured in the same way as the connecting studs of a cartridge. The line system can be flushed using the short-circuit bar.

What is claimed is:

1. Cartridge holder for a dialyzing machine for fastening and connecting a cartridge (11;18) comprising a tubular cartridge body (25) and two connecting studs (26,27) laterally projecting from the cartridge body, said cartridge holder having a holding element (35) retaining the cartridge and a clamping element (36) movable relatively to the holding element and radially to the retained cartridge, the clamping element (36) being movable from a closed position into an open position and comprising two connecting members (41,42) cooperating with lateral connecting studs (26,27) of the cartridge, the connecting members (41,42) sealingly engaging with the two connecting studs (26,27) when the clamping element (36) is moved into the closed position.

2. Cartridge holder according to claim 1, wherein the clamping element (36) consists of a rigid structure connected via links (40) with the holding element (35) so as to be movable in parallel.

3. Cartridge holder according to claim 1, wherein the holding element (35) comprises holding openings (46,47) for engaging with the connecting studs (26,27).

4. Cartridge holder according the claim 3, wherein the holding openings (46,47) are configured as keyhole openings and the connecting studs (26,27) comprise grooves (29) which are fittingly received in the slot (48) of the keyhole openings.

5. Cartridge holder according to claim 1, wherein the clamping element (36) is movable via a swivel bar (50;70) articulated to the holding element (35), the swivel bar (50;70) locking the inserted cartridge when the former is in its closed position.

6. Cartridge holder according to claim 5, wherein the swivel bar (50;70) surrounds the inserted cartridge (11;18) from three sides when the former is in the closed condition.

7. Cartridge holder according to claim 5, wherein the swivel bar (50) comprises an axial connecting member (54) which sealingly engages with an axial connecting stud (33) of the cartridge (11) when the swivel bar is moved into the closed position.

8. Cartridge holder according to claim 7, wherein the holding element (35) comprises a supporting device (55) at the end opposite the swivel bar (50), the supporting device (55) having another connecting member (56) for an axial connecting stud (33) of the cartridge (11).

9. Cartridge holder according to claim 1, wherein the clamping element (36) is adjustable in length for adjustment to cartridges of different sizes.

10. Cartridge holder according to claim 1, wherein the holding element (35) is fastened via a swivel device (76) to the dialyzing machine, the swivel device (76) allowing the inserted cartridge (18) to be tilted about a horizontal transverse axis.

11. Cartridge holder according to claim 5, wherein a sensor (60) is provided which detects the closed position of the swivel bar (50) and allows the dialyzing machine to be operated only when the swivel bar is closed.

* * * * *